United States Patent [19]

Arakawa et al.

[11] Patent Number: 4,622,954

[45] Date of Patent: Nov. 18, 1986

[54] ENDOSCOPE HAVING A PLATE-LIKE IMAGE SENSOR FOR FORMING IMAGES

[75] Inventors: Satoshi Arakawa; Makoto Toyota; Fumitaka Takeshita, all of Oomiya, Japan

[73] Assignee: Fuji Photo Optical Co., Ltd., Japan

[21] Appl. No.: 730,998

[22] Filed: May 6, 1985

[30] Foreign Application Priority Data

May 15, 1984 [JP] Japan ................................. 59-97233
May 15, 1984 [JP] Japan ................................. 59-97234
May 18, 1984 [JP] Japan ................................. 59-72790

[51] Int. Cl.<sup>4</sup> ............................................. A61B 1/04
[52] U.S. Cl. ........................................... 128/6; 358/98
[58] Field of Search .................... 128/6, 4; 358/98

[56] References Cited

U.S. PATENT DOCUMENTS 4,491,865  1/1985  Danna et al. ........................... 358/98
4,519,391  5/1985  Murakoshi .......................... 128/4 X
4,562,831  1/1986  Murakoshi et al. ..................... 128/6
4,573,450  3/1986  Arakawa ............................... 128/6

Primary Examiner—William H. Grieb
Attorney, Agent, or Firm—Parkhurst & Oliff

[57] ABSTRACT

An endoscope includes in the viewing head of its insertable section into a cavity of a living body an image sensor for generating a video signal which in turn is transmitted to a television display to be visualized thereon as a television picture. The image sensor with a shape such as a plate is located in a plane containing the longitudinal center line of the viewing head. The location permits to keep the shape of the viewing head unchanged. In addition, the image sensor thus located the interior of the viewing head into two spaces, one accommodating therein a forceps channel, and the other accommodating therein an objective lens assembly, resulting in a most efficient arrangement of essential elements for endoscope.

5 Claims, 2 Drawing Figures

ENDOSCOPE HAVING A PLATE-LIKE IMAGE SENSOR FOR FORMING IMAGES

BACKGROUND OF THE INVENTION

1. Field of the Invention

The present invention relates to an endoscope, and more particularly to an endoscope which has as an image pick-up device a plate like image sensor disposed within a viewing head thereof.

2. Description of the Prior Art

In addition to endoscopes having an optical fiber bundle as its image guide means, there have been proposed TV endoscopes of a type having as an image pick-up device an image sensor such as a charge coupled device (CCD) which comprises a great number of small photosensitive elements (pixels) arranged in a matrix. Such TV endoscopes, which are far better than endoscopes heretofore used considering from the standpoints of durability, the effect of video signal management and production cost, are in the improvement stage for practical application.

Image sensors now available, although which are miniaturized owing to recent progress in semiconductor production technology, specifically to the increase of integrating density, are too large in size to be incorporated within endoscopes. That is because endoscopes should be made with a small diameter for the purpose of insertion into a cavity of a living body. For example, a gastro-endoscope has its outer diameter of approximately ten (10) mm at the most. If image sensors now available, are miniaturized to a considerable degree suitable for being incorporated into endoscopes, there is left pending the problem of resolution. The requirement of improving resolution will require an image sensor to have an increased number of pixels, resulting in an increase in size.

With these points in background, it becomes very important how to arrange both an image sensor and an objective lens assembly forming directly optical image on the image sensor in a narrow space inside the viewing head of an endoscope. There will be considerations, one being that if an endoscope is of a front view type, an image sensor plate is placed parallel to a plane intersecting perpendicular to the longitudinal axis of the viewing head, and the other being that if an endoscope is of a side view type, an image sensor plate is placed close to the inside wall and along the longitudinal axis of the viewing head, It is, however, very difficult to make such an arrangement. The reason is that if it is a front view type of endoscope, considering a cross section of the viewing head, the image sensor plate occupies the majority of the cross section, making it difficult to incorporate essential elements such as light guide means, a forceps channel and an air and water supplying channel in the viewing head. In case of a side view type of endoscope, an objective lens assembly also occupies a cross section of the viewing head because it is placed close to the inside wall opposite to the image sensor plate so as to form an optical image onto the image sensor, resulting in the same difficulty as mentioned above. In addition, it is foreseen to deform the shape of either the image sensor plate or the viewing head when placing the plate like image sensor close to the inside wall of the viewing head having a circular cross section.

SUMMARY OF THE INVENTION

It is therefore an object of the present invention to provide an endoscope having a viewing head in which an image sensor can be arranged without any deformation of either the image sensor plate or the viewing head.

It is another object of the present invention to provide an endoscope having a viewing head in which an image sensor plate can be arranged without increasing the diameter of the viewing head.

According to the present invention, there is provided inside the viewing head of an endoscope an image sensor plate placed in a plane which contains the longitudinal axis of the viewing head. Such arrangement of image sensor plate permits to incorporate an image sensor plate having a size substantially matching the diameter of the viewing head. Furthermore, the arrangment of an image sensor plate permits to incorporate an image sensor plate having a required size without increasing the diameter of the viewing head.

In addition, according to the present invention, an image sensor thus arranged can divide the space inside the viewing head into two parts, one being allotted for at least a forceps channel and the other for an objective lens assembly which requires a relatively large space. As a result, the viewing head can accommodate many essential elements of an endoscope therein without any deformation thereof.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts through the figures thereof and wherein.

DETAILED DESCRIPTION OF THE PREFERRED EMBODIMENT

Description will hereunder be given of the preferred embodiment of an endoscope according to the present invention with reference to the accompanying drawings.

Figure 1:
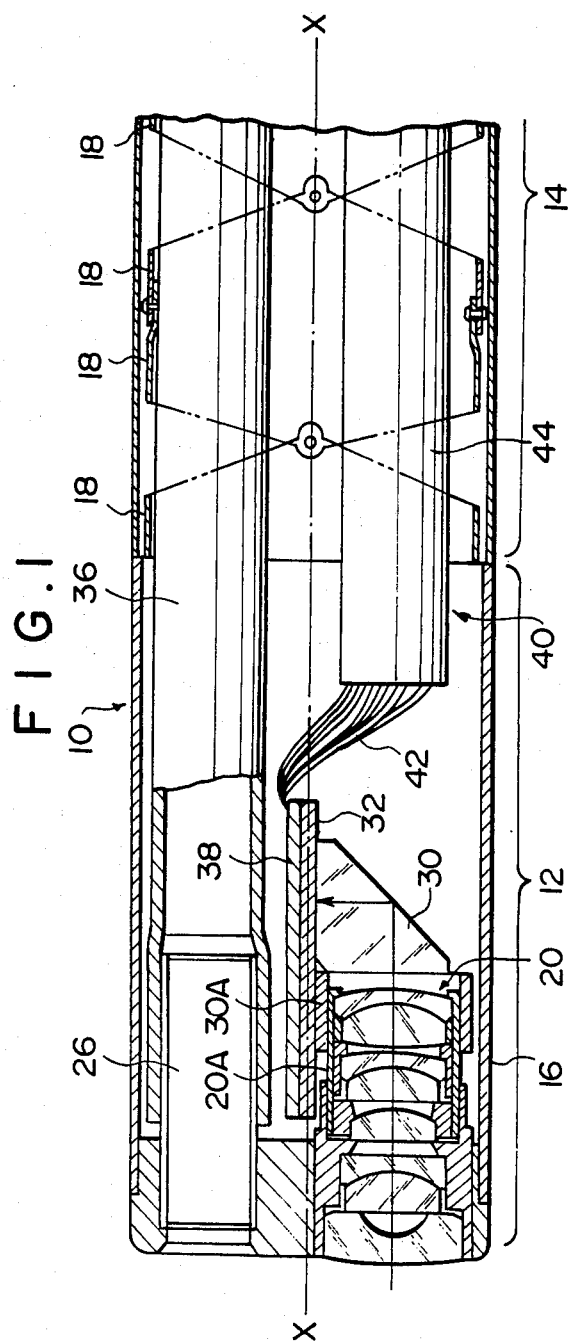
FIG. 1 is a longitudinal sectional view of an embodiment in which the present invention is applied to a front view type of endoscope.
Figure 2:
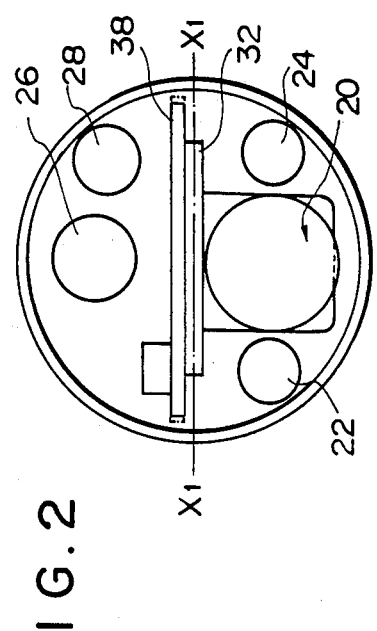
FIG. 2 is a schematic cross sectional view of the endoscope shown in FIG. 1.

Referring now to drawings, shown therein in sectional form, is an embodiment in which the present invention is applied to a front view type of endoscope having a flexible section insertable into a cavity of a living body including in its forward end portion 10 a viewing head 12 and intermediate bendable part 14. The viewing head 12, which has a metal barrel 16, is unflexible. But the bending part 14, comprising a chain of rings 18 articulated to one another which is flexed in desired directions by the operation of flexure controlling wires (not shown) in a manner well known in the art. As shown in FIG. 2, there are incorporated within the forward end portion 10, various elements such as light guide means 22 and 24, a forceps channel 26 and an air and water supplying channel 28 as well as an objective lens assembly 20, each element extending along the longitudinal axis of the flexible section (that is, the horizontal direction in FIG. 1). As apparent from FIG. 1, in the rear of the objective lens assembly 20 generally comprising plural elements, there is provided a right-angled prism 30 for turning the optical axis of the objective lens assembly 20 at a right angle. The prism 30 has a light emitting surface to which a plate like, rectangular image sensor 32 is cemented To ease the mounting of the objective lens assembly 20 into the viewing head 12, the following procedure should be taken. Before mounting, at first, the prism 30 is fixed to the image sensor plate 32 by using a proper jig in such a manner that the direction of the prism 30 coincides with the line of the arrangement of picture elements (pixels) of the image sensor 32 and then cemented together with a bonding agent. With moving a lens barrel 20A which holds the objective lens assembly 20 therein, back and forth in a fixed barrel 30A, the objective lens assembly 20 is adjusted so as to form a focused image on the image sensor plate 32, while coinciding the optical axis of the objective lens assembly 20 with the optical axis of the prism 30. After the completion of such adjustments, the lens barrel 20A is fixed to the fixed barrel 30A with, for example, a bonding agent so that an optical and positional correlation is maintained between the objective lens assembly 20 and the image sensor plate 32. As a result, such elements are incorporated as an image pick-up unit. The image pick-up unit is inserted into the metal barrel 16 and then located in its correct position where presenting on a television display a predetermined size of picture of an object at a certain distance away from the top end of the metal barrel 16. The locating operation is effected by moving the image pick-up unit back and forth in the metal barrel while looking at the picture presented on the television display. It is, of course, essential to place the image pick-up unit with its optical axis parallel to the center line X—X of the metal barrel 16.

The arrangement of image pick-up unit above-mentioned, permits to locate the image sensor plate 32 close to a plane containing the center line (shown by the line X—X in Figs.1 and X1—X1 in FIG. 2), making it possible to use the limited space effectively. It should be noted that if a dustproof construction is not required, it is not always necessary to cement the image sensor plate 32 to the prism 30. Therefore, other elements, for example a lens, a masking member and the like may be disposed, therebetween. In addition, the prism 30 may be substituted by a reflection mirror disposed at about a right angle.

Provided in the metal barrel 16 are various channels, for example, a forceps channel 26 coupled to a guide tube 36 through which a forceps is inserted into a cavity. As apparent from FIGS. 1 and 2, a seating plate 38 to which the image sensor plate 32 is fixed, has a width (in the direction of a diameter of the metal barrel), a little more than the width of the image sensor plate and a length (in the longitudinal direction of the metal barrel) substantially equal to the length thereof. Lead wires 40, each one being connected to a single photosensitive element (pixel) of the image sensor, are fixed at their ends to the seating plate 38. As well known in the art, the lead wires 40 serve to transmit driving signals from a control unit (not shown) to the image sensor 32 and video signals generated by the image sensor 32 to the control unit. The lead wires, which are comprised of very thin wires, have a loosened section 42 adjacent to the fixed end to the seating plate and a bundled section 44 covered with a sheath tube. As seen in FIG. 1, the entire loosened section 42 and part of the bundled section 44 are included in the metal inflexible barrel 12 so that every wire of the loosened section 42 is prevented from snapping. The interior of the metal barrel 16 is divided into two, upper and lower compartments with the image sensor plate 32 as a boundary partition, the upper one including therein the forceps channel 26 and the other the image pick-up unit and the lead wires 40 behind the unit. The arrangement of the image sensor plate 32 in a plane containing the longitudinal center line X—X of the metal barrel 16 permits the use of an image sensor with a high density of integration without increasing the diameter of metal barrel. Furthermore, the space in the metal barrel 16 divided into upper and lower compartments makes it easy to arrange the forceps channel 26 and the image pick-up unit separately. In addition, the lead wires 40, which are located in a space behind the unit in the lower compartment are prevented from interfering with other longitudinal members such as the light guide means 22 and 24.

According to the endoscope of the present invention constructed as described above, beside enabling the use of an image sensor plate with its short side of a size substantially equal to the diameter of the top of the insertion section of endoscope, the upper compartment divided by the image sensor plate is available as a space separated from the image pick-up unit, therefore the degree of freedom in arranging therein a forceps channel, an air and water supplying channel and the like is greatly increased.

In addition, according to the endoscope of the invention constructed as described above, the lower compartment divided by the image sensor plate in which the image pick-up unit is disposed provides a space behind the unit available for disposing the lead wires 40 without any interference from other members.

Furthermore, the lead wires 40, which are desired to be kept away as far as possible from the forceps channel 26 through which a high fequency knife is inserted to perform surgical operations, are permitted to be located in a space separated from the space where the forceps channel 26 is laid. The separation of the lead wires 40 from the forceps channel 26 prevents video signals from receiving any noises arising due to high frequency. The very thin wires 40 at the losened section 42 are prevented from snapping by locating the loosened section 42 in the metal barrel 16.

While the present invention has been described relating to a front view type of endoscope, it is equally applicable to other types of endoscopes.

Although a particular embodiment of the invention has been shown and described, it will be obvious to those skilled in the art that changes and modifications may be made without departing from the invention in its aspects, and therefore, the aim in the appended claims is to cover the true spirit and scope of the invention.

What is claimed is:
1. An endoscope having in the forward end portion of its insertable section into a cavity of a living body, an image sensor for generating a video signal which in turn is transmitted to a television display to be vizualized thereon as a television picture, said endoscope comprising:
   a plate like image sensor placed in a plane containing the longitudinal axis of said forward end portion of endoscope;
   a forceps channel disposed in one of spaces into which the interior of said forward end portion is divided by said plate like image sensor; and an objective lens assembly disposed in the other of said spaces.

2. An endoscope as defined in claim 1, further comprising lead wires connected to said plate like image sensor, said lead wires being located behind said objective lens assembly in said other space.

3. An endoscope as defined in claim 2, wherein said forward end portion comprises a flexible part and an inflexible part, said inflexible part including therein a loosened section of said lead wires.

4. An endoscope having in the forward end portion of its insertable section into a cavity of a living body an image sensor for generating a video signal which in turn is transmitted to a television display to be visualized thereon as a television picture, said endoscope comprising image pick-up means including an objective lens assembly disposed as one side thereof, a prism for turning an optical path and a plate like image sensor as a unit, said plate like image sensor being located in a plain containing the longitudinal center line of said insertable section of endoscope, said prism being fixed to said plate like image sensor and said objective lens assembly being movable relative to said prism so as to effect focus adjustment and optical axis alignment.

5. An endoscope as defined in claim 4, wherein said image pick-up means is fixed to said forward end portion after optically adjusted by a relative movement to said forward end portion.

* * * * *